US00PP13262P2

(12) United States Plant Patent
Heuver

(10) Patent No.: US PP13,262 P2
(45) Date of Patent: Nov. 19, 2002

(54) HARDY GREEN ASH TREE NAMED 'HEUVER'

(75) Inventor: Henry J. M. Heuver, Calgary (CA)

(73) Assignee: Bailey Nurseries, Inc., St. Paul, MN (US)

( * ) Notice: Subject to any disclaimer, the term of this patent is extended or adjusted under 35 U.S.C. 154(b) by 0 days.

(21) Appl. No.: 09/578,687

(22) Filed: May 26, 2000

(51) Int. Cl.[7] ..... A01H 5/00
(52) U.S. Cl. ..... Plt./219
(58) Field of Search ..... Plt./219, 216

(56) References Cited

U.S. PATENT DOCUMENTS

PP3,385 P * 8/1973 Klehm et al. ..... Plt./219
PP7,120 P * 1/1990 Wandell ..... Plt./219
PP8,077 P * 12/1992 Zampini ..... Plt./219

* cited by examiner

*Primary Examiner*—Kent L. Bell
(74) *Attorney, Agent, or Firm*—Burns, Doane, Swecker & Mathis, L.L.P.

(57) ABSTRACT

An attractive male Green Ash tree is provided that exhibits extreme winter hardiness. An oval crown is formed that tends to be denser and more compact than that of the 'Patmore' variety (U.S. Plant Pat. No. 4,684). The branch angles generally are greater than those of the 'Patmore' variety. The leaflets are glossy dark green and generally display less serration than the 'Patmore' variety. Also, the bark generally is smoother than that of the 'Patmore' variety particularly when young. The new variety is well suited for growing as a street planting or an ornamental shade tree in the landscape.

7 Drawing Sheets

SUMMARY OF THE INVENTION

The new variety of *Fraxinus pennsylvanica lanceolata* was discovered and selected during August 1987 while growing among Green Ash seedlings at Vegreville, Alberta, Canada. At the time of the discovery, the new variety was present among Green Ash trees planted in the late 1970's using a hardy seed source from Montana. During the selection it was desired to provide a Green Ash tree that is hardier than the 'Patmore' variety (U.S. Plant Pat. No. 4,684) since severe winter damage and kill has been observed for such variety in the Prairie Provences of Canada. The Calgary area where the selection was made is recognized to be one of the harshest winter climates in North America. Other selection criteria included an attractive growth habit and ovarall tree shape, freedom from seed formation, and attractive glossy leaves. Had the new variety of the present invention not been discovered and preserved it would have been lost to mankind.

It was found that the new variety of the present invention:

(a) Exhibit greater winter hardiness than the 'Patmore' variety,
(b) Forms no seeds,
(c) Forms glossy dark green leaflets having generally less serration than the 'Patmore' variety,
(d) Exhibits when young a generally smoother bark than the 'Patmore' variety,
(e) Exhibits an oval crown that is generally more dense and compact than that of the 'Patmore' variety, and
(f) Is particularly well suited for growing as a street planting or a shade tree in the landscape.

Trees of the new variety were first asexually reproduced by budding on *Fraxinus pennsylvanica lanceolata* rootstock at Kelowna, British Columbia, Canada. The new variety also has been asexually reproduced at Saint Paul, Minn. The characteristics of the new variety have been found to be strictly transmissible from one generation to another following such asexual reproduction. The plant has proven to be very stable through a number of years of asexual propagation by budding. There have been observed no variants or off types to date.

The new variety has been demonstrated to possess slightly less vigor than the 'Patmore' variety. At a given age the caliper will be approximately the same as the 'Patmore' variety; however, the new variety is shorter and more compact. At times it may be desirable to thin the branches of the new variety to limited extent. The height of the new variety at a given age will tend to be shorter than that of the 'Patmore' variety. The more dense and compact growth habit and generally rounder head of the new variety will convey a superior overall appearance than the more open growth habit of the 'Patmore' variety. The winter hardiness of the new variety has also been found to be significantly greater than that of the 'Patmore' variety.

The new variety of the present invention initially was designated the 'Foothills' variety. It subsequently has been named the 'Heuver' variety.

BRIEF DESCRIPTION OF THE PHOTOGRAPHS

The accompanying photographs show as true as it is reasonably possible in color illustrations of this nature, plants and plant parts of the new variety of the present invention. Similar photographs of the 'Patmore' variety are provided for comparative purposes. The trees were grown at Kelowna, British Columbia, Canada, and were photographed during August, 1999 except as indicated for FIGS. 3 and 4.

DETAILED DESCRIPTION

Figure 1:
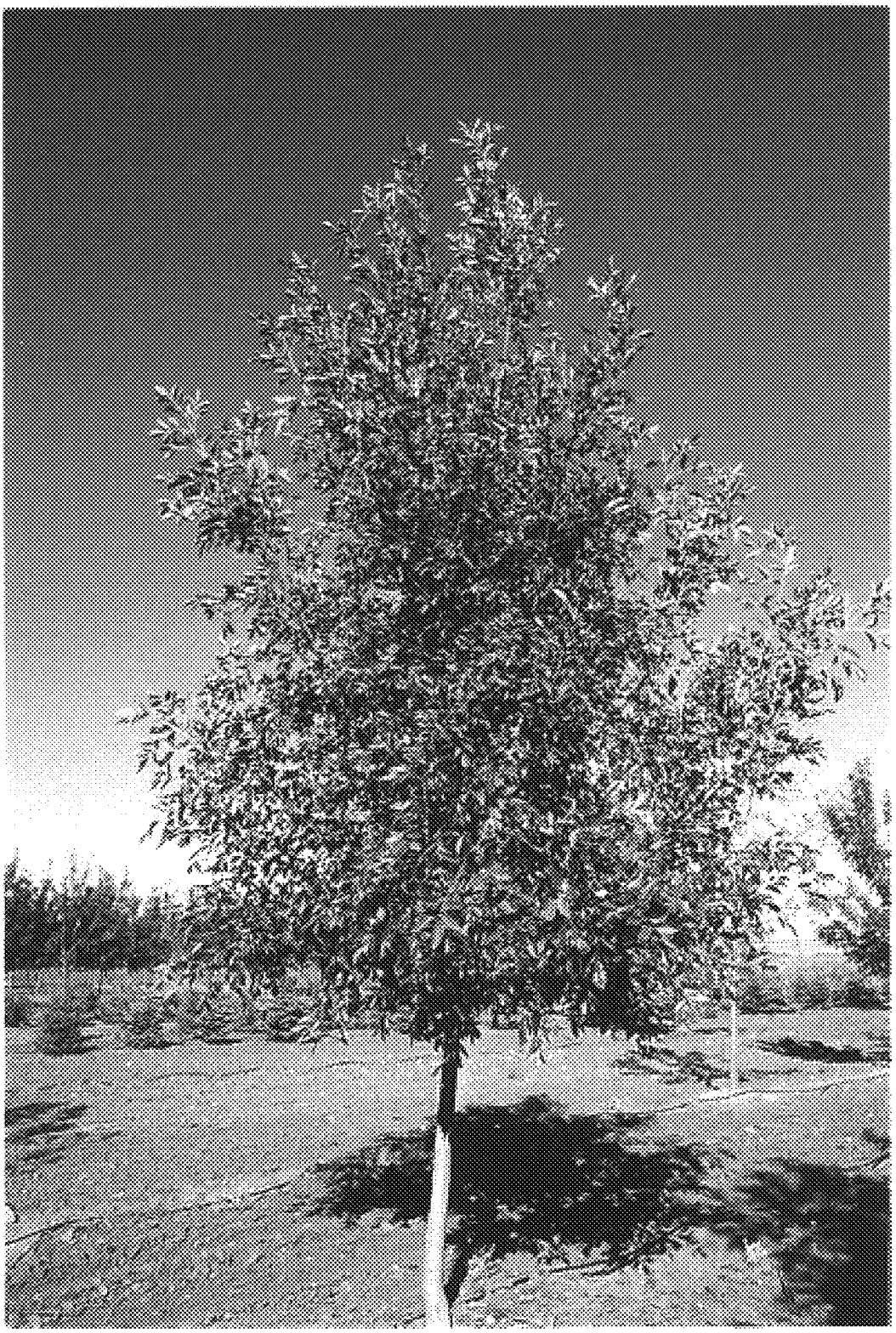
FIG. 1 shows a typical entire tree of the 'Heuver' variety wherein the relatively dense and compact growth habit is illustrated.
Figure 2:
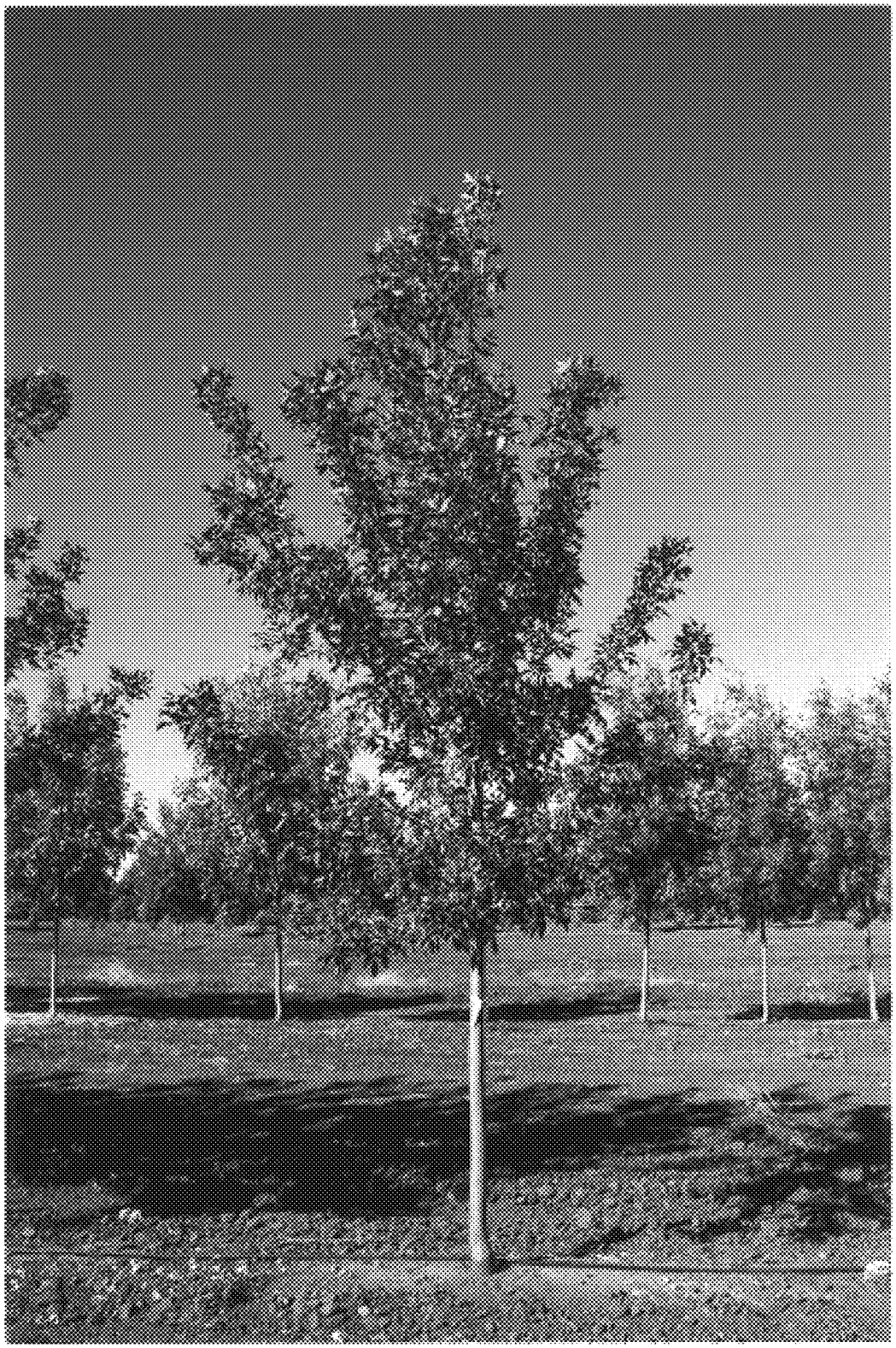
FIG. 2 shows for comparative purposes a typical entire tree of the 'Patmore' variety wherein a more open growth habit is illustrated.
Figure 3:
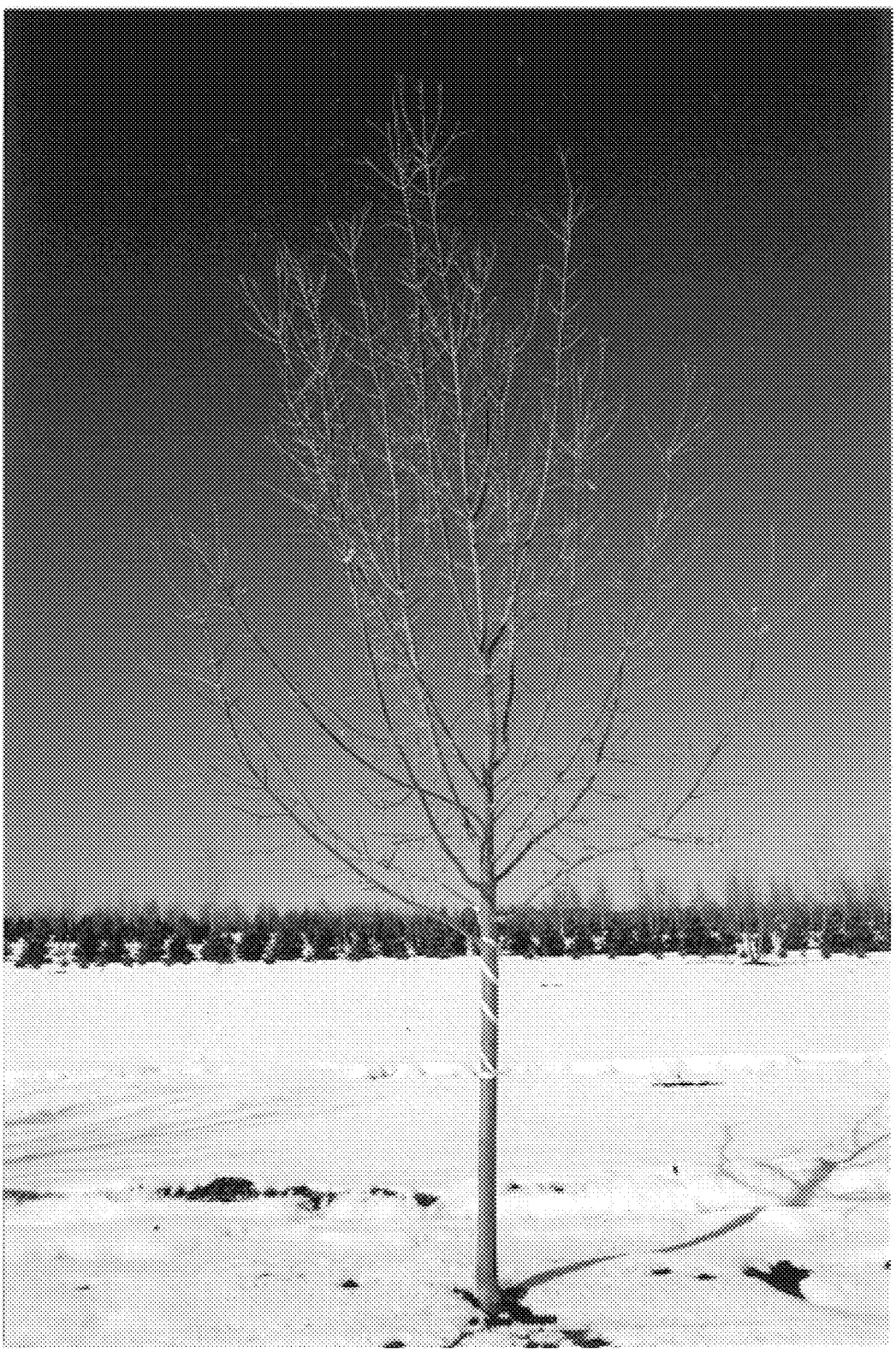
FIG. 3 illustrates a typical entire tree of the 'Heuver' variety during January, 2000 wherein the relatively dense branch concentration is illustrated.
Figure 4:
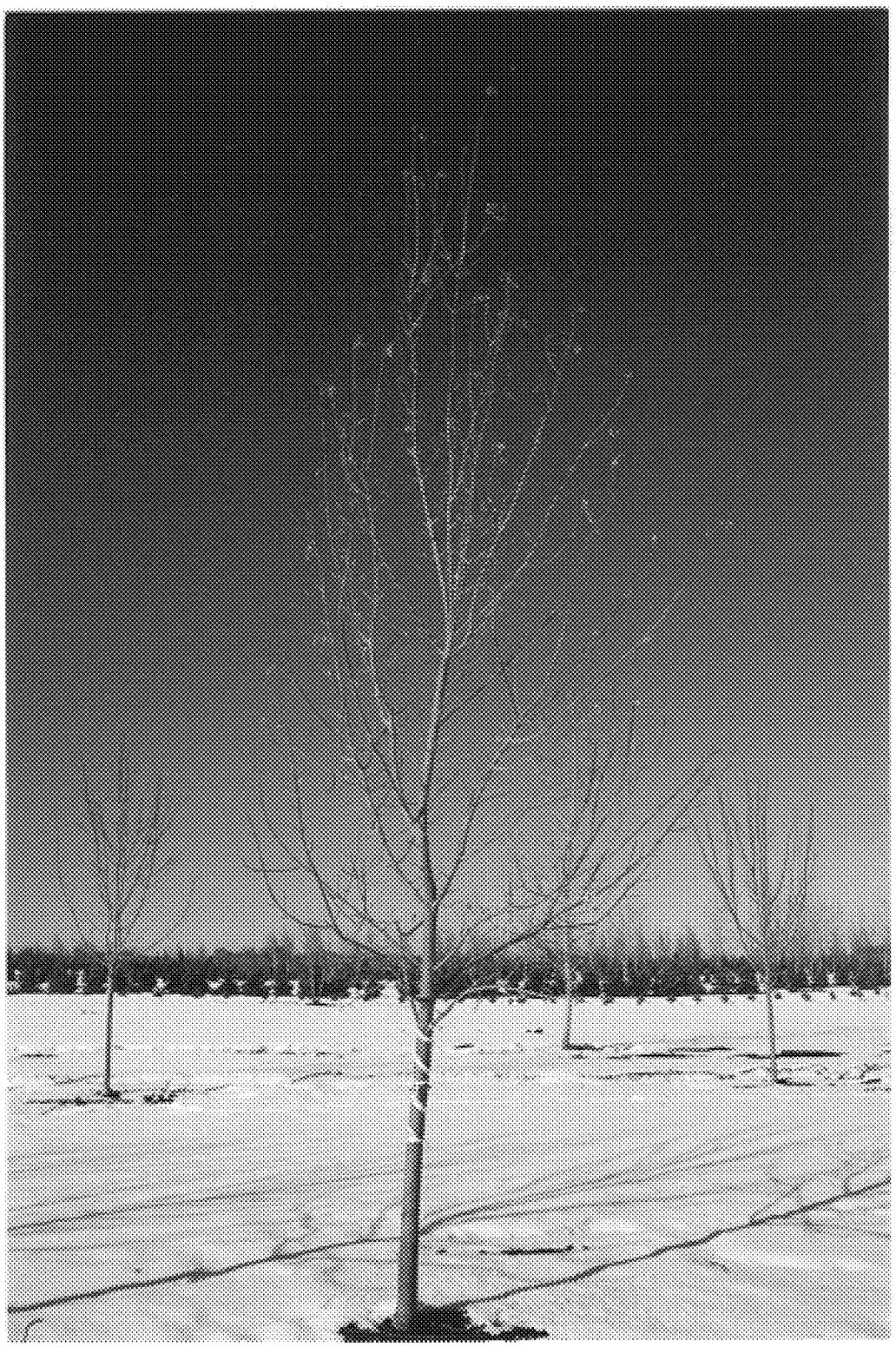
FIG. 4 illustrates a typical entire tree of the 'Patmore' variety during January, 2000 wherein the somewhat more open presentation of branches is illustrated.

The chart used in the identification of colors is that of The Royal Horticultural Society, London (R.H.S. Colour Chart). Other reference to color is to be accorded its ordinary dictionary significance. The description is based upon the inspection of budded trees of the new variety of approximately seven years of age while growing in the field at Kelowna, British Columbia, Canada.

Botanical classification: *Fraxinus pennsylvanica lanceolata*, cv. 'Heuver'.

Parentage: A seedling of unknown parentage.

Propagation: It holds its distinguishing characteristics well through asexual reproduction by budding on seedling ash rootstock.

Tree:

*Vigor.*—Slightly less vigorous than the 'Patmore' variety.

*Size.*—A one year-old whip of the new variety has a height of approximately 5 to 7 feet. A three-year-old tree of the new variety has a height of approximately 10 to 12 feet and a spread of approximately 4 to 6 feet. A five-year-old tree of the new variety has a height of approximately 14 to 16 feet and a spread of approximately 8 to 10 feet. When compared to the 'Patmore' variety a one year-old tree commonly is approximately 1 foot shorter, a three year-old tree commonly is approximately 1½ to 2 feet shorter, a five year-old tree commonly is approximately 3 feet shorter, and a ten year-old tree commonly is approximately 4 feet shorter. Such dimensions are for trees that are budded on standard *Fraxinus pennsylvania* understock. The oldest known tree of the new variety is approximately 11 years of age and has a height of approximately 25 feet and a spread of approximately 12 feet.

*Growth habit.*—Upright oval. The crown tends to be fuller, more uniform, more rounded and more compact and dense than that of the 'Patmore' variety.

*Branch angle.*—Tends to be somewhat greater and more flattened than the 'Patmore' variety. For instance, branch angles of approximately 45 degrees commonly are displayed by the new variety. This can be compared to branch angles of approximately 30 degrees for the 'Patmore' variety.

*Bark.*—Near Greyed-Green Group 198D, and relatively smooth on young trees. Such bark on young trees is considerably smoother than that of the 'Patmore' variety. Also, the bark appears to be more resistant to sun scald than that of the 'Patmore' variety. The bark coloration is substantially the same as that of the 'Patmore' variety.

*Caliper.*—Substantially the same as that of the 'Patmore' variety for a given age. Four-year-old trees commonly display a trunk diameter of approximately 2 inches, five-year-old trees commonly display a trunk diameter of approximately 2.5 inches, six-year-old trees commonly display a trunk diameter of approximately 3 inches, and seven-year-old trees commonly display a trunk diameter of approximately 4 inches.

*Hardiness.*—Well suited for growing in U.S.D.A. Hardiness Zones 2 to 6. Has well withstood temperatures of −40° F. with no injury. Under such climatic conditions severe damage has been experienced by the 'Patmore' variety.

*Disease resistance.*—The resistance and susceptibility to disease are believed to be generally comparable to that of other *Fraxinus pennsylvania* varieties. The improved winter hardiness of the new variety enables the handling of cold with less stress and may translate to some improved disease resistance as well. However, any improved disease resistance requires further confirmation.

*Insect resistance.*—The resistance and susceptibility to insects are believed to be generally comparable to that of other *Fraxinus pennsylvania* varieties. However, the improved winter hardiness may yield a stronger overall tree that better resists damage by insects. Such improved insect resistance requires further confirmation.

Foliage characteristics:

*Configuration.*—Pinnately compound, narrow elliptic, with a narrow cuneate base and an acuminate tip.

*Size.*—Typical dimensions for an overall leaf are a length of approximately 27.7 cm and a width of approximately 24.7 cm. A typical leaflet width is approximately 5.9 cm.

*Leaf appearance.*—Glossy on upper surface.

Figure 5:
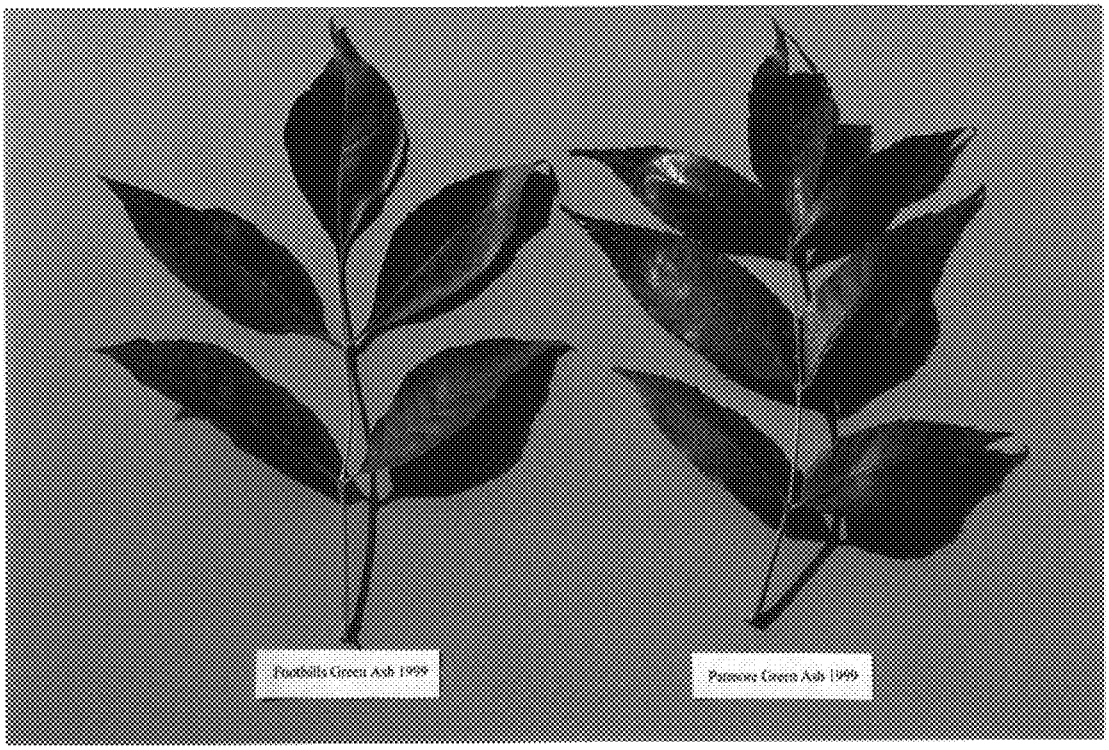
FIG. 5 illustrates the upper surfaces of typical glossy dark green leaves of the 'Heuver' variety (left) and the 'Patmore' variety (right). The serration at the margins of the leaflets is more pronounced on the 'Patmore' variety.
Figure 6:
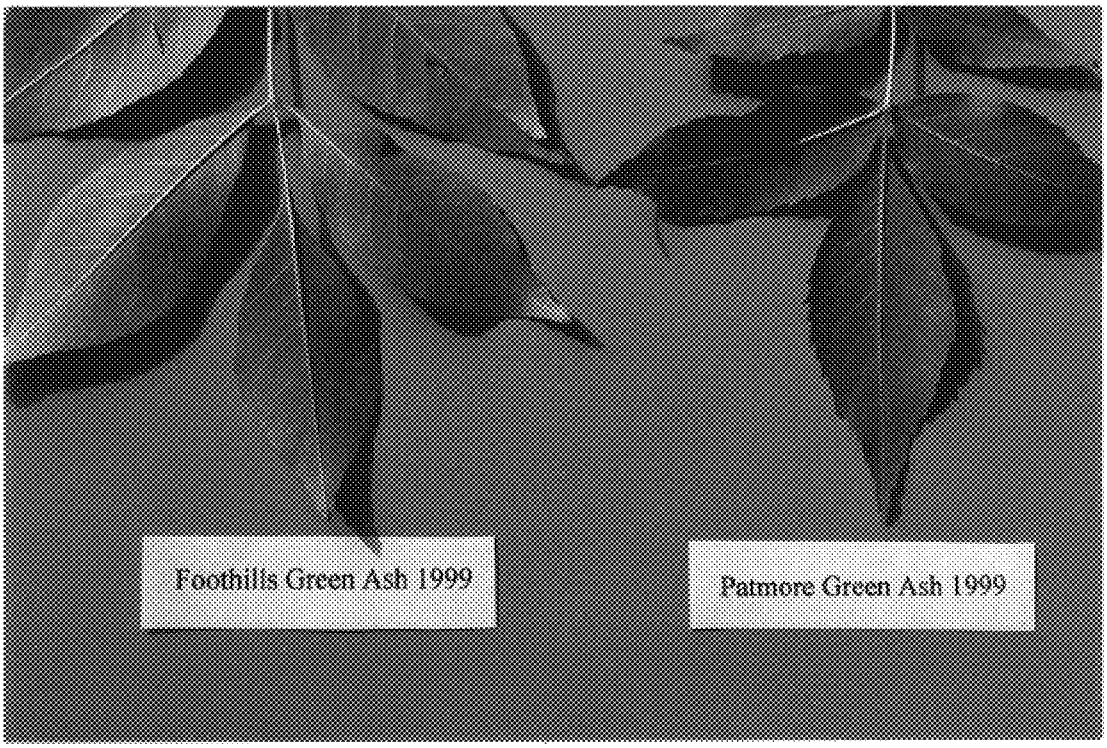
FIG. 6 illustrates the under surfaces of typical leaves of the 'Heuver' variety (left) and the 'Patmore' variety (right). The serration at the margins of the leaflets is more pronounced on the 'Patmore' variety.
Figure 7:
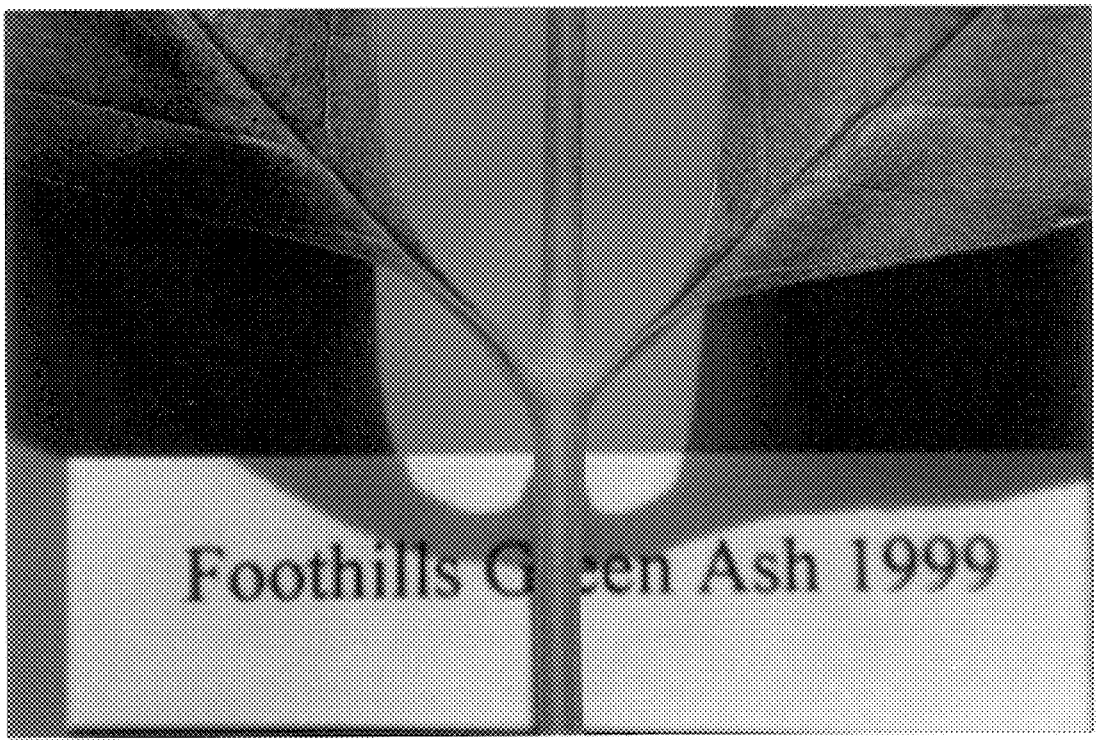
FIG. 7 illustrates the upper surface of typical leaves (partially shown), leaf stem and petiolules of the 'Heuver' variety. The absence of the serration on the margins of the leaflets near the base is illustrated.
Figure 8:
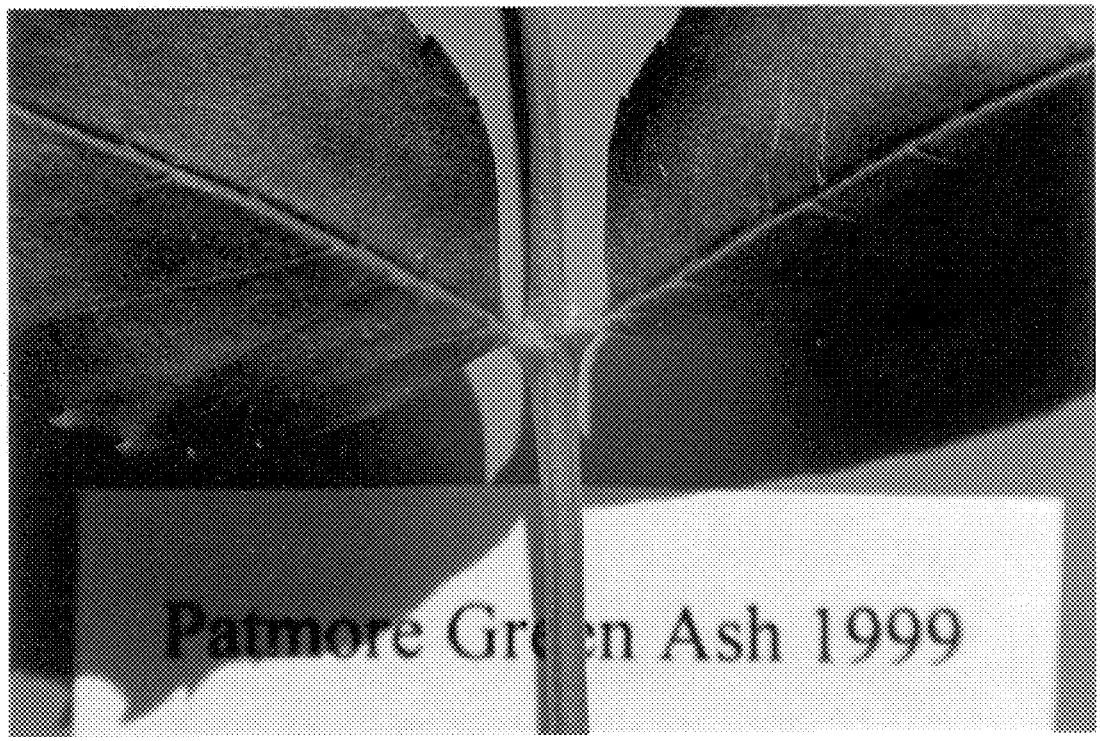
FIG. 8 illustrates the upper surface of typical leaves (partially shown), leaf stem and petiolules of the 'Patmore' variety. The petiolules are considerably shorter than illustrated in FIG. 7 for the 'Heuver' variety and some serration is visible at the margins of the leaflets.
Figure 9:
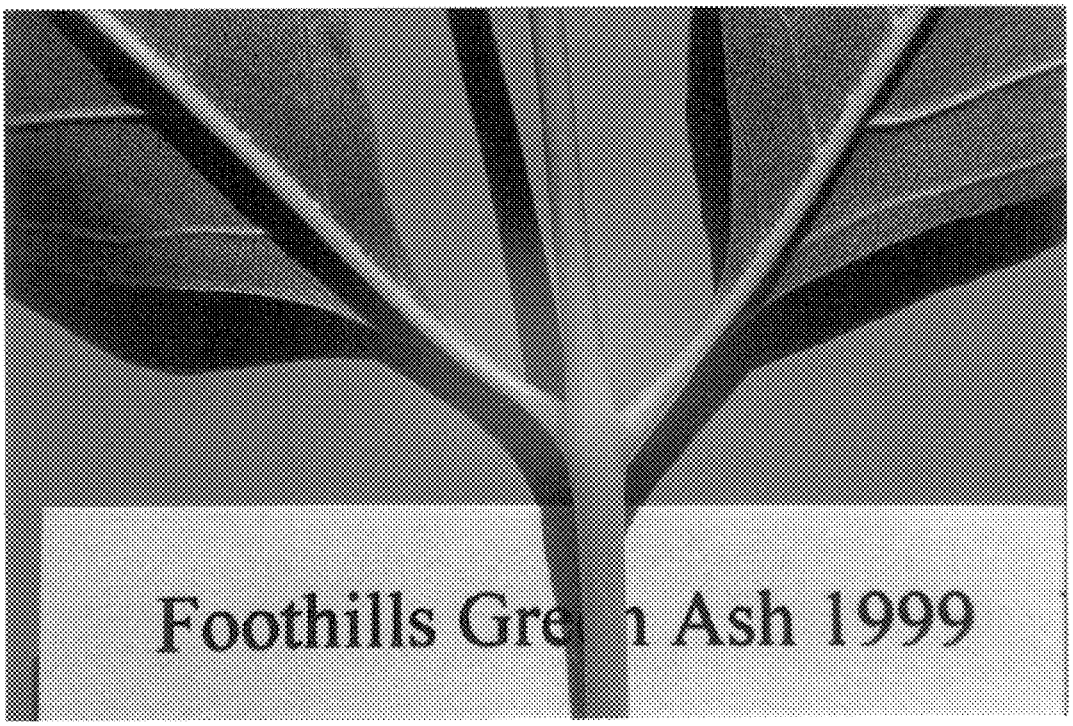
FIG. 9 illustrates the under surface of typical leaves (partially shown), leaf stem and petiolules of the 'Heuver' variety. Once again, the absence of serration on the margins of the leaflets near the base is visible.
Figure 10:
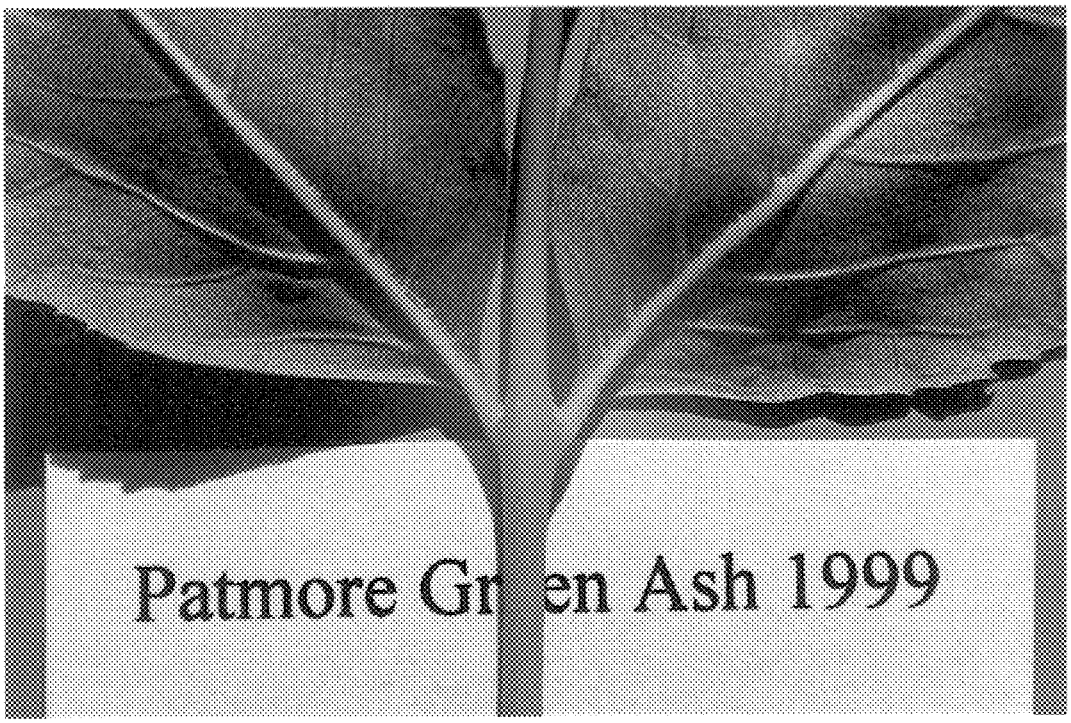
FIG. 10 illustrates the under surface of typical leaves (partially shown), leaf stem and petiolules of the 'Patmore' variety. Leaf serration and short petiolules are apparent that are lacking in the comparable FIG. 9 of the 'Heuver' cultivar.

*Serration.*—Minimal and considerably less pronounced than the 'Patmore' variety. See FIGS. 5, 6, 7, 8, 9, and 10 in this regard.

*Leaflet color.*—Dark green, near Yellow-Green Group 146A on the upper surface when observing two year-old trees in September of 1999. Veins are lighter green in coloration (as illustrated). Yellow leaves are displayed in the fall.

*Leaflet number.*—Five or seven per leaf.

*Leaflet length.*—Commonly approximately 10 to 12 cm.

*Leaf stems.*—Light green.

*Leaf petioles and petiolules.*—Light green, not winged, round in cross section, pubescence is absent or sparse, and the petiole commonly measures approximately 5.6 cm in length.

*Pubescence.*—Some along the mid-rib near base on lower surface.

Flowers: The flowers are consistently staminate, formed on old wood just below new shoots, small to medium in size, a calyx is present and a corolla is absent, lacking in fragrance, and are borne in a panicle. Flowers commonly appear approximately one week earlier than on the 'Patmore' variety. No seeds have been observed.

I claim:

1. A new and distinct variety of *Fraxinus pennsylvanica lanceolata* plant which exhibits the following combination of characteristics:

(a) Exhibits greater winter hardiness than the 'Patmore variety' (U.S. Plant Pat. No. 4,684), (b) Forms no seeds, (c) Forms glossy dark green leaflets having generally less serration than the 'Patmore' variety, (d) Exhibits when young a generally smoother bark than the 'Patmore' variety, (e) Exhibits an oval crown that is generally more dense and compact than that of the 'Patmore' variety, and (f) Is particularly well suited for growing as a street planting or as a shade tree in the landscape:

substantially as herein shown and described.

* * * * *